US007150188B2

(12) United States Patent
Charara et al.

(10) Patent No.: US 7,150,188 B2
(45) Date of Patent: Dec. 19, 2006

(54) NON-INVASIVE MEASUREMENT OF FLUID-PRESSURE DIFFUSIVITY USING ELECTRO-OSMOSIS

(75) Inventors: Marwan Charara, Rueil Malmaison (FR); Steven Pride, Moraga, CA (US); Patrice Ligneul, Princeton, NJ (US)

(73) Assignee: Schlumberger Technology Corporation, Sugar Land, TX (US)

( * ) Notice: Subject to any disclaimer, the term of this patent is extended or adjusted under 35 U.S.C. 154(b) by 148 days.

(21) Appl. No.: 11/014,325

(22) Filed: Dec. 16, 2004

(65) Prior Publication Data
US 2006/0130573 A1 Jun. 22, 2006

(51) Int. Cl.
E21B 47/06 (2006.01)
G01V 3/02 (2006.01)

(52) U.S. Cl. ............... 73/152.05; 73/152.17; 73/152.46; 73/152.51; 73/152.53; 324/366; 324/367; 324/370

(58) Field of Classification Search ............ 73/152.02, 73/152.05, 152.17, 152.46, 152.51–152.53; 324/366–374
See application file for complete search history.

(56) References Cited

U.S. PATENT DOCUMENTS

| 2,814,017 | A |   | 11/1957 | Doll |              |
|-----------|---|---|---------|------|--------------|
| 3,566,682 | A | * | 3/1971  | Winkler, Jr. | ............... 73/152.14 |
| 3,599,085 | A |   | 8/1971  | Semmelink |        |
| 4,427,944 | A |   | 1/1984  | Chandler |         |
| 4,468,623 | A | * | 8/1984  | Gianzero et al. | ............ 324/367 |
| 4,904,942 | A |   | 2/1990  | Thompson |         |
| 5,162,740 | A | * | 11/1992 | Jewell | ........................ 324/347 |
| 5,345,179 | A | * | 9/1994  | Habashy et al. | ............. 324/338 |
| 5,417,104 | A |   | 5/1995  | Wong |             |
| 5,689,068 | A | * | 11/1997 | Locatelli et al. | ......... 73/152.02 |
| 5,841,280 | A |   | 11/1998 | Yu et al. |        |
| 5,877,995 | A |   | 3/1999  | Thompson et al. |  |
| 6,225,806 | B1 |  | 5/2001  | Millar et al. |   |
| 6,597,633 | B1 | * | 7/2003  | Millar et al. | ................... 367/35 |
| 6,653,839 | B1 | * | 11/2003 | Yuratich et al. | ............ 324/355 |
| 6,998,845 | B1 | * | 2/2006  | Martin et al. | ............... 324/346 |
| 2002/0043977 | A1 | * | 4/2002 | Vail, III | ...................... 324/368 |
| 2004/0196046 | A1 | * | 10/2004 | Aidan et al. | ................ 324/339 |
| 2005/0116709 | A1 | * | 6/2005  | Proett et al. | ................ 324/303 |
| 2005/0174119 | A1 | * | 8/2005  | Ligneul et al. | ............. 324/337 |

* cited by examiner

Primary Examiner—Hezron Williams
Assistant Examiner—David A. Rogers
(74) Attorney, Agent, or Firm—Victor H. Segura; Brigitte L. Echols

(57) ABSTRACT

An apparatus for determining fluid-pressure diffusivity in a borehole (12) in a formation (10) includes an electrode (16) and a strain measuring device (18),(20) (or a particle velocity measuring device (18),(20) or a particle acceleration measuring device (18),(20)) disposed a fixed distance from the electrode (16). The electrode (16) injects an electrical current into a point on a wall of the borehole (12). The strain measuring device (18),(20) measures strain (or the particle velocity measuring device (18),(20) measuresd particle velocity or the particle acceleration measuring device (18),(20) measures particle acceleration) at the fixed distance from the point of injection of the electrical current over time. The fluid-pressure diffusivity is determined based on the measured strain (or measured particle velocity or measured particle acceleration) over time. A method of determining a fluid-pressure diffusivity in a borehole (12) includes injecting an electrical current into a point on a wall of the borehole (12), measuring at least one of strain, particle velocity, and particle acceleration at a fixed distance from the point of injection of the electrical current over time, and determining the fluid-pressure diffusivity based on the measured at least one of strain, particle velocity, and particle acceleration over time.

32 Claims, 9 Drawing Sheets

Fig. 2 - PRIOR ART

NON-INVASIVE MEASUREMENT OF FLUID-PRESSURE DIFFUSIVITY USING ELECTRO-OSMOSIS

BACKGROUND OF INVENTION

1. Field of the Invention

The invention relates generally to well logging of Earth boreholes and, more particularly, to a method and apparatus for determining the properties of subsurface rock such as fluid-pressure diffusivity of porous media.

2. Background Art

U.S. Pat. No. 3,599,085 describes a method in which a sonic source is lowered down a borehole and used to emit low frequency sound waves. Electrokinetic effects in the surrounding fluid-bearing rock cause an oscillating electric field in this and is measured at least two locations close to the source by contact pad touching the borehole wall. The ratio of the measured potentials being related to the electrokinetic skin depth to provide an indication of permeability of the formation.

U.S. Pat. No. 4,427,944 describes a method which injects fluid at high pressure of alternating polarity to the formation and measurement of the generated transient streaming potentials in the time domain to estimate the characteristic response time which is inversely proportional to the formation permeability.

U.S. Pat. No. 2,814,017 describes a method where by measuring of the difference in phase between periodic pressure waves passed through a formation and potentials generated by the oscillatory motion of the formation caused by these pressure waves and, conversely, application of a periodically varying electric current to the formation fluid to generate periodic pressure waves in the formation by electro-osmosis. Measurements of the phase shift in the frequency domain between the generating and generated quantities is said to be a measure of permeability of formation.

U.S. Pat. No. 5,417,104 describes a method whereby sound waves of fixed frequency are emitted from a downhole source and the resulting electrokinetic potentials measured. An electrical source of fixed frequency is then used to produce electro-osmotic signals and the acoustic response measured. Using both responses together, the permeability is then deduced, provided the electrical conductivity of the rock is also separately measured.

U.S. Pat. No. 4,904,942 describes several arrangements for recording electrokinetic signals from subsurface rocks mainly with the electrodes measuring the signals at or close to the earth's surface but including use of acoustic source mounted on a downhole tool. There is no indication of permeability being deduced. A further related (inverse) method is described in U.S. Pat. No. 5,877,995, which contains several arrangements for setting out electrical sources and acoustic receivers (geophones) in order to measure electro-acoustic signals induced in subsurface rocks.

U.S. Pat. No. 6,225,806 describes an apparatus for enhancing the seismo-electric measurements where a seismic source with two frequencies radiates radially a seismic signal within the borehole and the electric signals are recorded by a pair of electrodes above and below the seismic source. This type of measurement is said to determine the permeability of the formation. These methods are unable to measure continuously the permeability of porous rock directly with accuracy from a downhole tool. Streaming potential measurements cannot cross easily the mudcake pressure barrier and cannot be used as a continuous logging tool as it needs to impose a big differential pressure and requires time for the pressure front to diffuse into the formation.

Electro-osmotic measurements are closely related to permeability see (U.S. Pat. No. 5,417,104); however, measuring the induced pressure field through the mudcake with a pressure gauge is not feasible because the mudcake is a pressure barrier.

SUMMARY OF INVENTION

In one or more embodiments, the present invention involves a method of determining a fluid-pressure diffusivity in a borehole comprising injecting an electrical current into a point on a wall of the borehole; measuring at least one of strain, particle velocity, and particle acceleration at a fixed distance from the point of injection of the electrical current over time; and determining the fluid-pressure diffusivity based on the measured at least one of strain, particle velocity, and particle acceleration over time. Further embodiments of the method may also include one or more of the following. The method further comprising measuring at least one of strain, particle velocity, and particle acceleration at a plurality of fixed distances from the point of injection of the electrical current over time; and determining the fluid-pressure diffusivity based on the plurality of measured at least one of strains, particle velocities, and particle accelerations over time. The method further comprising mounting an electrode on a pad; mounting a measurement device on the pad a fixed distance from the electrode; disposing the pad against the wall of the borehole to facilitate the electrode injecting the electrical current and the measurement device measuring at least one of strain, particle velocity, and particle acceleration. The method further comprising mounting a second measurement device on the pad a second fixed distance from the electrode; disposing the pad against the wall of the borehole to facilitate the second measurement device measuring at least one of strain, particle velocity, and particle acceleration. The determining of the fluid-pressure diffusivity comprises locating a point in time at which a second time derivative of the measured at least one of strain, particle velocity, and particle acceleration is zero. The at least one of strain, particle velocity, and particle acceleration is measured with a Doppler-shifted laser displacement sensor. The at least one of strain, particle velocity, and particle acceleration is measured with a piezo ceramic transducer. A waveform of the injected current is a simple step function. The injected current is 0.1 A. The fixed distance is 2 cm.

In one or more embodiments, the present invention involves an apparatus for determining a fluid-pressure diffusivity in a borehole comprising an electrode; and a measurement device disposed a fixed distance from the electrode; wherein the electrode injects an electrical current into a point on a wall of the borehole, wherein the measurement device measures at least one of strain, particle velocity, and particle acceleration at the fixed distance from the point of injection of the electrical current over time; and wherein the fluid-pressure diffusivity is determined based on the measured at least one of strain, particle velocity, and particle acceleration over time. Further embodiments of the apparatus may also include one or more of the following. The apparatus further comprising a second measurement device disposed a second fixed distance from the electrode; wherein the second measurement device measures at least one of strain, particle velocity, and particle acceleration at the second fixed distance from the point of injection of the electrical current over time; and wherein the fluid-pressure diffusivity is determined based on the second measured at least one of strain, particle velocity, and particle acceleration over time. The electrode and the measurement device are mounted on a pad. The measurement device, and the second measurement device are mounted on a pad. The determining of the fluid-pressure diffusivity comprising locating a point in time at which a second time derivative of the measured at least one of strain, particle velocity, and particle acceleration is zero. The measurement device is a Doppler-shifted laser displacement sensor. The measurement device is a piezo ceramic transducer. A waveform of the injected current is a simple step function. The injected current is 0.1 A. The fixed distance is 2 cm.

In one or more embodiments, the present invention involves an apparatus for determining a fluid-pressure diffusivity in a borehole comprising means for injecting an electrical current into a point on a wall of the borehole; and means for measuring at least one of strain, particle velocity, and particle acceleration at a fixed distance from the point of injection of the electrical current over time; wherein the fluid-pressure diffusivity is determined based on the measured at least one of strain, particle velocity, and particle acceleration over time. Further embodiments of the apparatus may also include one or more of the following. The apparatus further comprising means for measuring at least one of strain, particle velocity, and particle acceleration at a plurality of fixed distances from the point of injection of the electrical current over time; and means for determining the fluid-pressure diffusivity based on the plurality of measured at least one of strains, particle velocities, and particle accelerations over time. The determining of the fluid-pressure diffusivity comprises locating a point in time at which a second time derivative of the measured at least one of strain, particle velocity, and particle acceleration is zero. A waveform of the injected current is a simple step function. The injected current is 0.1 A. The fixed distance is 2 cm.

In one or more embodiments, the present invention involves a logging tool for determining a fluid-pressure diffusivity in a borehole comprising an electrode mounted on a pad; and a measurement device mounted on the pad a fixed distance from the electrode; wherein the pad is disposed against a wall of the borehole so as to facilitate the electrode injecting an electrical current into a point on a wall of the borehole and the measurement device measures at least one of strain, particle velocity, and particle acceleration at the fixed distance from the point of injection of the electrical current over time; wherein the electrode injects an electrical current into the point on a wall of the borehole; wherein the measurement device measures at least one of strain, particle velocity, and particle acceleration at the fixed distance from the point of injection of the electrical current over time; and wherein the fluid-pressure diffusivity is determined based on the measured at least one of strain, particle velocity, and particle acceleration over time; and wherein the determining of the fluid-pressure diffusivity comprises locating a point in time at which a second time derivative of the measured at least one of strain, particle velocity, and particle acceleration is zero. Further embodiments of the logging tool may also include one or more of the following. The measurement device is a Doppler-shifted laser displacement sensor. The measurment device is piezo ceramic transducer. A waveform of the injected current is a simple step function. The injected current is 0.1 A. The fixed distance is 2 cm.

Other aspects and advantages of the invention will be apparent from the following description and the appended claims.

DETAILED DESCRIPTION

Figure 1:
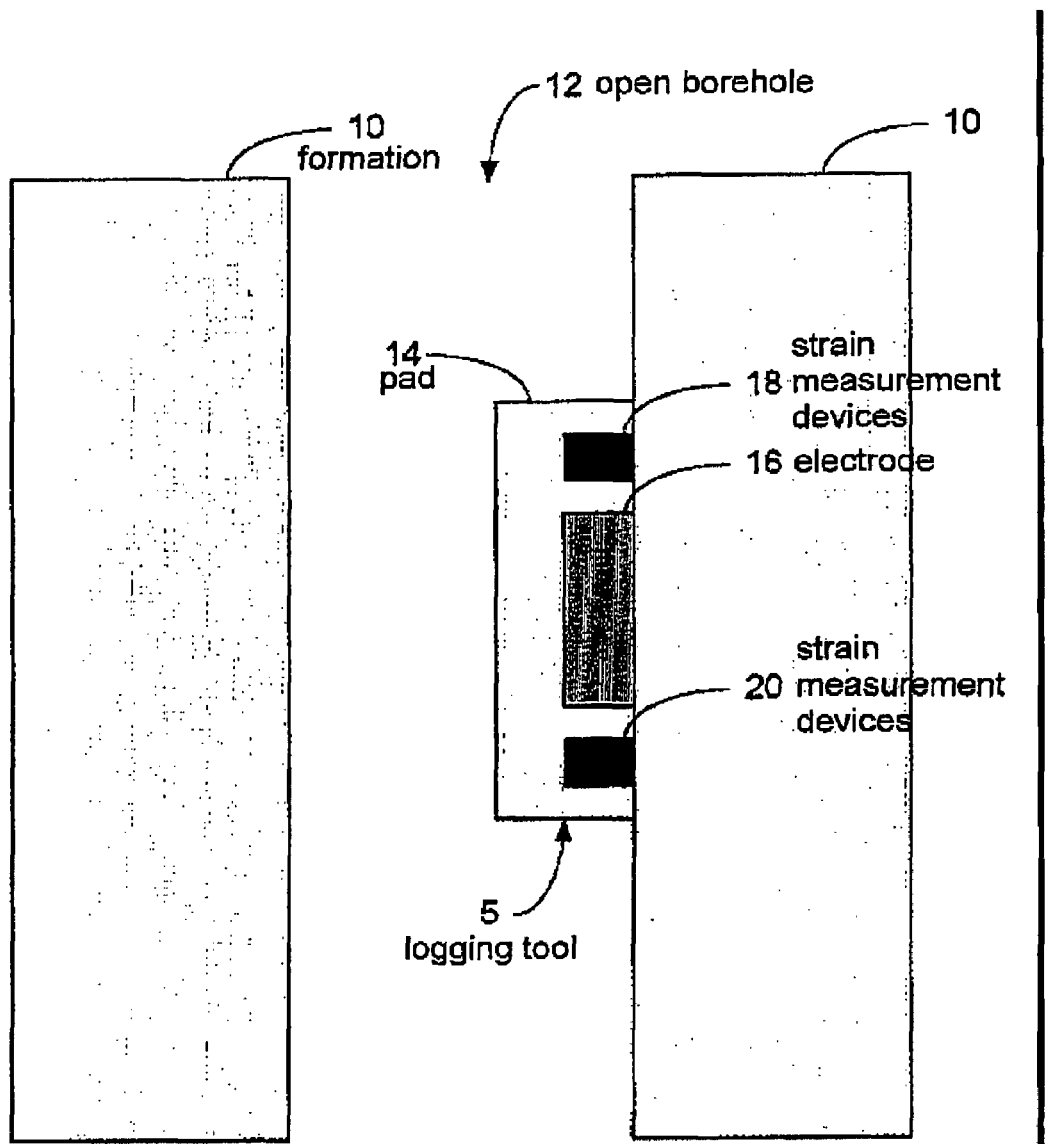
FIG. 1 shows a logging tool in accordance with one or more embodiments of the present invention.

The present invention will be described in detail with reference to the drawings.

Like reference numerals are used to denote like items throughout the various figures.

The invention relates generally to well logging of Earth boreholes and, more particularly, to a method and apparatus for determining the properties of subsurface rock such as diffusivity of porous media.

Referring to FIG. 1, a logging tool (5) for making electro-osmotic measurements in a formation (10) in an open borehole (12) is shown. In one or more embodiments, the logging tool (5) includes a pad (14), which is capable of being mounted against the wall of the borehole (12). The pad (14) includes an electrode (16) and strain measurement devices (18),(20). The electrode (16) is capable of injecting electrical current into the borehole wall. The strain measurement devices (18),(20) are capable of measuring the displacement, or the strain, with respect to time. Those skilled in the art will appreciate that the strain measurement devices (18),(20) may be classical displacement or strain gauges or more efficient sensors, such as Doppler-shifted laser beams or piezo ceramic transducer used for micro/nano positioning.

Those skilled in the art will appreciate that the logging tool described above may take many forms and may be constructed in many ways. Additionally, the logging tool could be incorporated into or onto other downhole equipment, and may involve other components, for example, to facilitate lowering the logging tool into the borehole, maintaining the logging tool in a position against the wall of the borehole, etc. Any such modifications may be incorporated without departing from the spirit of the present invention In one or more embodiments, the above a method for determining the diffusivity of the formation relies on inversion, i.e., minimizing the misfit function between the synthetic data (computed through numerical modeling of (Eq. 13) set forth below with the appropriate set of boundary conditions) and the acquired data. The algorithm is iterative and needs initial guess values. An estimate of the diffusivity of the formation can be obtained by using the method detailed in the Practical Example presented below. The method to determine the fluid-pressure diffusivity/permeability involves locating the point in time at which the second time derivative of either displacement or strain goes to zero. This time depends on the fluid pressure diffusivity of the material and the known distance from the injection point to strain/displacement measurements. The measurement of the inflection point in time provides a rapid (less than milliseconds) non-invasive means for measuring the fluid-pressure diffusivity of the porous material.

Practical Example

Below, the principles involved in the method of one or more embodiments of the present invention are presented together with a practical consideration of a simple interface. Those skilled in the art will appreciate from the below that the principles presented also apply to a real borehole, and that the fluid-pressure diffusivity in a real borehole, while more complex, is similarly computable.

ElectroKinetic Phenomenon

Figure 2:
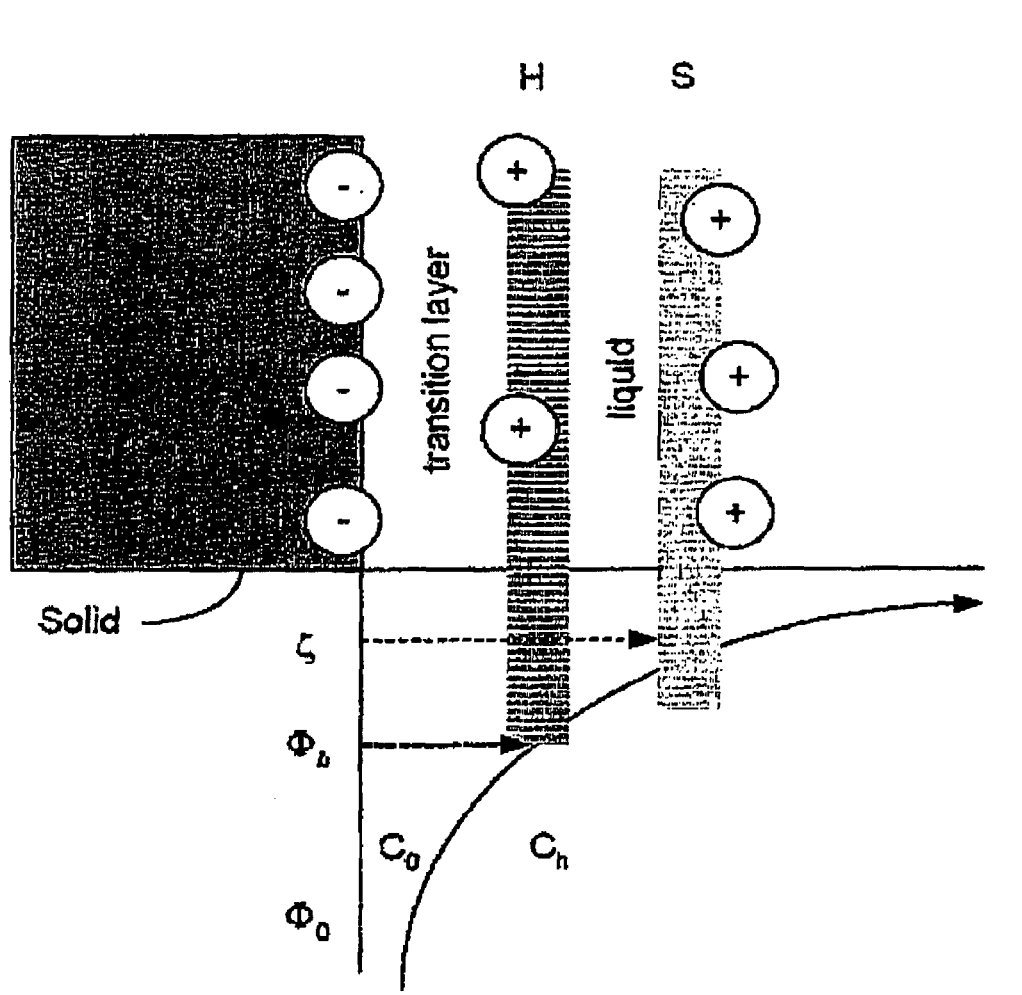
FIG. 2 shows a representation of the Electrokinetic Phenomenon.

As can be seen in FIG. 2, when a porous medium contains an electrolyte, depending on the electric potential ("Zeta potential $\zeta$") between the solid grains and the liquid, cations for instance have the tendency to become chemically bound to the solid grain boundaries leaving a layer of free anions to move in the pore fluid adjacent to the solid surfaces. The immobile bound charge on the grain surfaces balanced by free counter charge in the adjacent fluid is called the electric double layer. Movement of the free counter charge relative to the bound surface charge is the source of all electrokinetic phenomena.

The scheme of the electrochemical solid/electrolyte interface can be modeled using Stern's model, in which: $C_0$ is the charge density of the rock-fluid surface zone, $\Phi_0$ is the surface potential, H is the plane between diffusive zone and adsorbed ions with a charge density $C_h$. S is the slipping plane with a corresponding $\zeta$ potential. $\Phi_h$ and $\zeta$ can be positive or negative.

Electro-osmosis is the phenomenon by which an applied electric field drives a fluid flow in water-saturated porous materials. This phenomenon is due to the presence of a charge separation (the electric double layer) present at the interface between water and solid surfaces such as silicate grains in rocks. A layer of charged surface sites and/or adsorbed ions on the grain surfaces is balanced by a diffuse layer of oppositely charged free ions in the liquid immediately adjacent to the grain surfaces. When an electric field is applied, it acts as a body force on the diffuse layer charge which results in fluid flow.

Response of a Half Space

Figure 3:
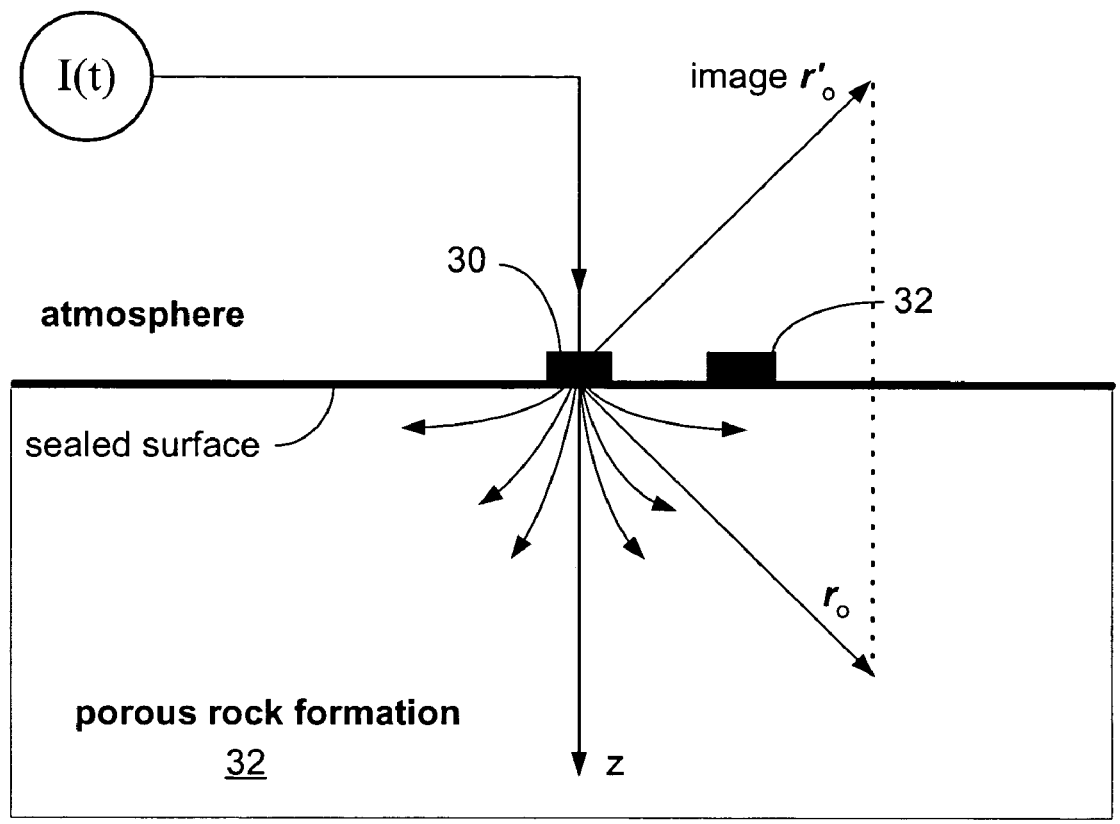
FIG. 3 shows an exemplary situation for measuring the response of a porous rock formation to an injected current.

In a single injection electrode modeled as a point source and located on the surface of the half space, the position of this electrode defines the origin of the coordinates. The porous material is assumed to be uniform and the surface is assumed to be sealed to fluid flow. An exemplary such situation is depicted in FIG. 3. The governing equations for this situation correspond to the quasi-static limit of the equations by Steven Pride (Steven Pride, 1994, *"Governing equations for the coupled electromagnetics and acoustic of porous media"*, Phys. Rev. B 50 (21), 15678–15696).

$$\nabla \cdot J = -I_0 f(t) \delta(r) \quad \text{(Eq. 1)}$$

$$\nabla \cdot \tau^D - \nabla P_c = 0 \quad \text{(Eq. 2)}$$

$$-J = \sigma \nabla \varphi + L \nabla p_f \quad \text{(Eq. 3)}$$

$$-\frac{\partial w}{\partial t} = L \nabla \varphi + \frac{k}{\eta} \nabla p_f \quad \text{(Eq. 4)}$$

$$-P_c = K_U \nabla \cdot u + C \nabla \cdot w \quad \text{(Eq. 5)}$$

$$-p_f = C \nabla \cdot u + M \nabla \cdot w \quad \text{(Eq. 6)}$$

$$\tau^D = G\left(\nabla \cdot u + \nabla \cdot u^T - \frac{2}{3} \nabla \cdot uI\right) \quad \text{(Eq. 7)}$$

In the situation shown in FIG. 3, an injection electrode (30) and strain gauge (32) are attached to the surface of a porous half space (34). The boundary conditions at the sealed interface separating the porous material from the insulating air in this example are that $\hat{z} \cdot J = 0$, $\hat{z} \cdot w = 0$, and $$\hat{z} \cdot (\tau^D - P_c I) = 0 \quad \text{(Eq. 8)}$$

where $\hat{z}$ is the outer normal to the interface. In a borehole application, the interface separating the fluid-filled borhole from the rock formation need not be electrically insulating; however, it will be impermeable ($\hat{z} \cdot w = 0$) due to the presence of either mudcake or a measurement pad that slides along sealing the interface. All fields approach zero at infinite distance from the source. The fields are the current density J, the fluid filtration displacement w (defined so that is $\partial w/\partial t$ is the Darcy velocity), the solid displacements u, the electrical potential $\phi$, the fluid pressure $p_f$, the confining pressure and the stress deviator $\tau^D$. The material properties are the electrokinetic coupling coefficient L, the porosity $\phi$, the poroelasticity incompressibilities $K_U$ (undrained bulk modulus), C, and M, the shear modulus G, the fluid viscosity $\eta$, the rock's electrical conductivity $\sigma$, and the rock permeability k. The constant $I_0$ is the injection current amplitude (coulombs/s) while the dimensionless time function $f(t)$ is able to be chosen. In this Practical Example, the simple step function with the step at t=0 will be used. Those skilled in the art will appreciate, however, that various alternate waveforms can be used without departing from the spirit of the present invention.

Induced Fluid-Pressure Variations

A simplification can be made by neglecting the influence of the electro-osmotic flow on the electrical current; i.e., the term $L\nabla p_f$ in (Eq. 3) is neglected. Such coupling is an $O(L^2)$ effect that is easily shown to be negligible. In this way, the problem for the electrical potential $\phi$ is completely decoupled from that for the fluid pressure. Thus, the electrical fields are controlled by the simple quasi-static Poisson problem.

$$\nabla^2 \varphi = \frac{I_0 f(t)}{\sigma} \delta(r) \quad \text{(Eq. 9)}$$

satisfying $\partial \phi / \partial z = 0$ on the surface (from (Eq. 8)). This problem has the well-known solution of a point-source potential located at r=0.

$$\varphi(r, t) = \frac{I_0 f(t)}{2\pi\sigma|r|} \quad \text{(Eq. 10)}$$

where $|r|=\sqrt{x^2+y^2+z^2}$. This expression for $\phi$ is twice the infinite whole-space response.

The poroelastic fluid-pressure response due to the current source is a Biot slow wave (i.e., pure fluid pressure diffusion) (See Biot, M. A., 1956, *"Theory of propagation of elastic waves in a fluid saturated porous solid. I. Low frequency range"*, J. Acoust. Soc. Am., 28, 168–178.). For a slow wave, the fluid accumulations $\nabla \cdot w$ and the dilatations $\nabla \cdot u$ are related as (See Steven Pride, 2003, *"Relationships between seismic and hydrological properties"*, In Hydrogeophysics, edited by Y. Rubin and S. Hubbard, PP. 1–31, Kluwer, N.Y.)

$$\nabla \cdot u = \frac{1}{\beta} \nabla \cdot w \quad \text{(Eq. 11)}$$

where $$\beta = \frac{K_U + 4G/3}{C} \quad \text{(Eq. 12)}$$

Thus, upon inserting the generalized Darcy law into the fluid pressure constitutive law, the fluid pressure diffusion equation is obtained $$D\nabla^2 p_f - \frac{\partial p_f}{\partial t} = -\frac{L}{\sigma}\frac{(C+M\beta)}{\beta}I_0 f(t)\delta(r) \quad \text{(Eq. 13)}$$

where the fluid pressure-diffusivity D is identified as $$D = \frac{k}{\eta}\left(M + \frac{C}{\beta}\right) \quad \text{(Eq. 14)}$$

This diffusion problem has the well-known solution (solve for the Green function by taking Fourier transforms and then convolve with the time function)

$$p_f(r, t) = \frac{2L(C+M\beta)I_0}{\sigma\beta}\int_\infty^t dt' f(t')\frac{\exp(-r^2/[4D(t-t')])}{[4\pi D(t-t')]^{3/2}} \quad \text{(Eq. 15)}$$

where $r=|r|$. Now, assuming that $f(t)$ is the simple unit step function that turns on at $t=0$, a change of time variables [$\frac{1}{4}D(t-t')=u^2$ where u is the new integration variable] allows the integral to be identified as the complimentary error function or, equivalently, as $$p_f(r, t) = \frac{L(C+M\beta)}{D\sigma\beta}\frac{I_0}{2\pi r}\left[1 - erf\left(\frac{x}{\sqrt{4Dt}}\right)\right] \quad \text{(Eq. 16)}$$

The error function is defined $$erf(y) = \frac{2}{\sqrt{\pi}}\int_0^y e^{-\zeta^2} d\zeta$$

and varies from 0 to 1 as its argument y (real) varies from 0 to $\infty$; for example, for y>2, we have that erf(y)$\approx$1.

Figure 4:
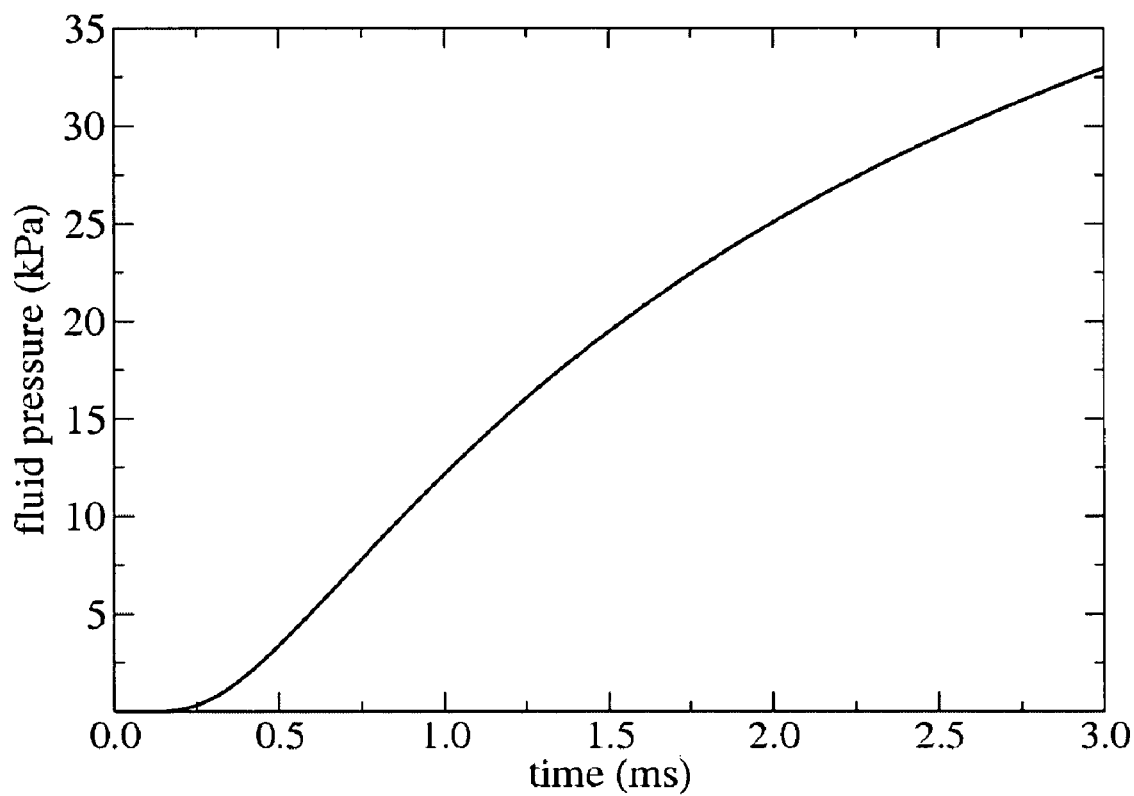
FIG. 4 shows, for a typical consolidated sandstone, a plot of the temporal evolution of the fluid pressure at an observation point.

FIG. 4 shows, for a typical consolidated sandstone, a plot of the temporal evolution of the fluid pressure at an observation point that is a distance $r_0=2$ cm from the current injection electrode (30). The current is a steady $I_0=0.1$ A. By measuring how the fluid pressure $p_f(r,t)$ evolves in time at some fixed distance r from the current injection point, one could deduce the fluid pressure diffusivity D. However, this would require an intrusive measurement of the fluid pressure.

Displacements and Strains at the Surface

So that no probes or tubes have to be inserted into material, how the displacement u and strain $\nabla u$ vary at a point (or points) on the surface $z=0$ is measured. Those skilled in the art will appreciate various ways of measuring the time derivatives of these fields, e.g., from using Doppler-shifted laser beams to a fixed strain gauge that measures $\partial u_z(r,t)/\partial r$ (the angular deflection of an initially horizontal line element at a point r on the surface). During the fluid pressure diffusion, it was already noted that $\nabla \cdot w = \beta \nabla \cdot u$ which from (Eq. 5) and the definition of $\beta$ gives the interesting result that $P_c = 4 G \nabla \cdot u/3$ (the confining pressure and volume dilatations are actually related by the shear modulus in a slow wave). Thus, for a slow wave, (Eq. 2) becomes $\nabla^2 u - \nabla\nabla \cdot u = 0$ and (Eq. 6) becomes $p_f = (C+M\beta) \nabla \cdot u$. The solid displacements induced by fluid-pressure diffusion are then governed by the Poisson problem $$\nabla^2 u = \frac{1}{C+M\beta}\nabla p_f \quad \text{(Eq. 17)}$$

And satisfy the free surface condition $\hat{z} \cdot (\tau^D - P_c I) = 0$ that may be written as $$\hat{z} \cdot \nabla u + \nabla u \cdot \hat{z} = 2\hat{z} \cdot \nabla u \quad \text{(Eq. 18)}$$

The vertical component of the displacement $u_z$ therefore is a solution of the well-posed problem $$\nabla^2 u_z = \frac{1}{C+M\beta}\frac{\partial p_f}{\partial z} \text{ throughout } z \geq 0 \quad \text{(Eq. 19)}$$

$$\frac{\partial u_z}{\partial z} = \frac{p_f}{C+M\beta} \text{ on } z = 0 \quad \text{(Eq. 20)}$$

Once $u_z$ is determined, the other components can be obtained using $$\nabla^2 u_x = \frac{1}{C+M\beta}\frac{\partial p_f}{\partial x} \text{ throughout } z \geq 0 \quad \text{(Eq. 21)}$$

$$\frac{\partial u_x}{\partial z} = -\frac{\partial u_z}{\partial x} \text{ on } z = 0 \quad \text{(Eq. 22)}$$

And similarly for the component (replace x by y).
To obtain $u_z$, a Green function satisfying $$\nabla^2 g = \delta(r - r_0) \text{ throughout } z \geq 0 \quad \text{(Eq. 23)}$$

$$\frac{\partial g}{\partial z} = 0 \text{ on } z = 0 \quad \text{(Eq. 24)}$$

is introduced. The usual self-adjoint operations (products, subtractions and integrations) are then performed on (Eq. 19) and (Eq. 23) and the boundary conditions of (Eq. 20) and (Eq. 24) applied to give $$(C + M\beta) u_z = \int_{z \geq 0} dV_0 p_f \frac{\partial g}{\partial z_0};$$

i.e., the surface integral is eliminated. Thus, upon introducing the pressure $p_f$ of (Eq. 16) we have $$(C + M\beta) u_z(r, t) = \quad \text{(Eq. 25)}$$
$$\int_{z \geq 0} dV_0 g(r - r_0) \frac{\partial p_f(r_0, t)}{\partial z_0} + \int_{z=0} dS_0 g(r - r_0) p_f(r_0, t)$$

If the volume integral is integrated by parts and Green's theorem applied (note that the outward normal to z=0 is $-\hat{z}$) one obtains that $$u_z(r, t) = \frac{LI_0}{2\pi\sigma\beta D} \int_{z \geq 0} \frac{dV_0}{r_0} \text{erfc}\left(\frac{r_0}{\sqrt{4Dt}}\right) \frac{\partial g}{\partial z_0} \quad \text{(Eq. 26)}$$

where $\text{erfc}(y) = 1 - \text{erf}(y)$ is the complementary function.

The Green function for Laplace's equation that satisfies a homogeneous Neumann condition on the surface is $$g(r - r_0) = \frac{1}{4\pi}\left\{\frac{1}{|r - r_0'|} + \frac{1}{|r - r_0'|}\right\} \quad \text{(Eq. 27)}$$

Where $r_0'$ is the image of the depth point $r_0$ as reflected about $z_0=0$ (see FIG. 1). Working in spherical coordinates $(r, \theta, \phi)$ where $\theta$ denotes latitude and $\phi$ longitude and considering the response at observation points r on the surface z=r cos θ=0 (i.e., θ=π/2 and along the arbitrary line φ=0, one obtains $$\left.\frac{\partial g}{\partial z_0}\right|_{z=0, \phi=0} = \frac{-r_0 \cos\phi_0}{2\pi [r^2 - 2rr_0 \sin\theta_0 \cos\phi_0 + r_0^2]^{3/2}} \quad \text{(Eq. 28)}$$

for source points $(r_0, \theta_0, \phi_0)$ throughout the half space.

Using the volume element $dV_0 = r_0^2 \sin\theta_0 dr_0 d\theta_0 d\phi_0$ in (Eq. 26) then gives that along observation line φ=0 on the free surface θ=π/2

$$u_z(r, t) = \frac{LI_0}{2\pi\sigma\beta D} \int_{-\pi}^{\pi} d\phi_0 \int_0^{\infty} dr_0 r_0^2 \text{erfc} \quad \text{(Eq. 29)}$$

-continued
$$\left(\frac{r_0}{\sqrt{4Dt}}\right) \int_0^{\pi/2} \frac{d\theta_0 \sin\theta_0 \cos\theta_0}{[r^2 + r_0^2 - 2rr_0 \sin\theta_0 \cos\phi_0]^{3/2}}$$

Figure 5:
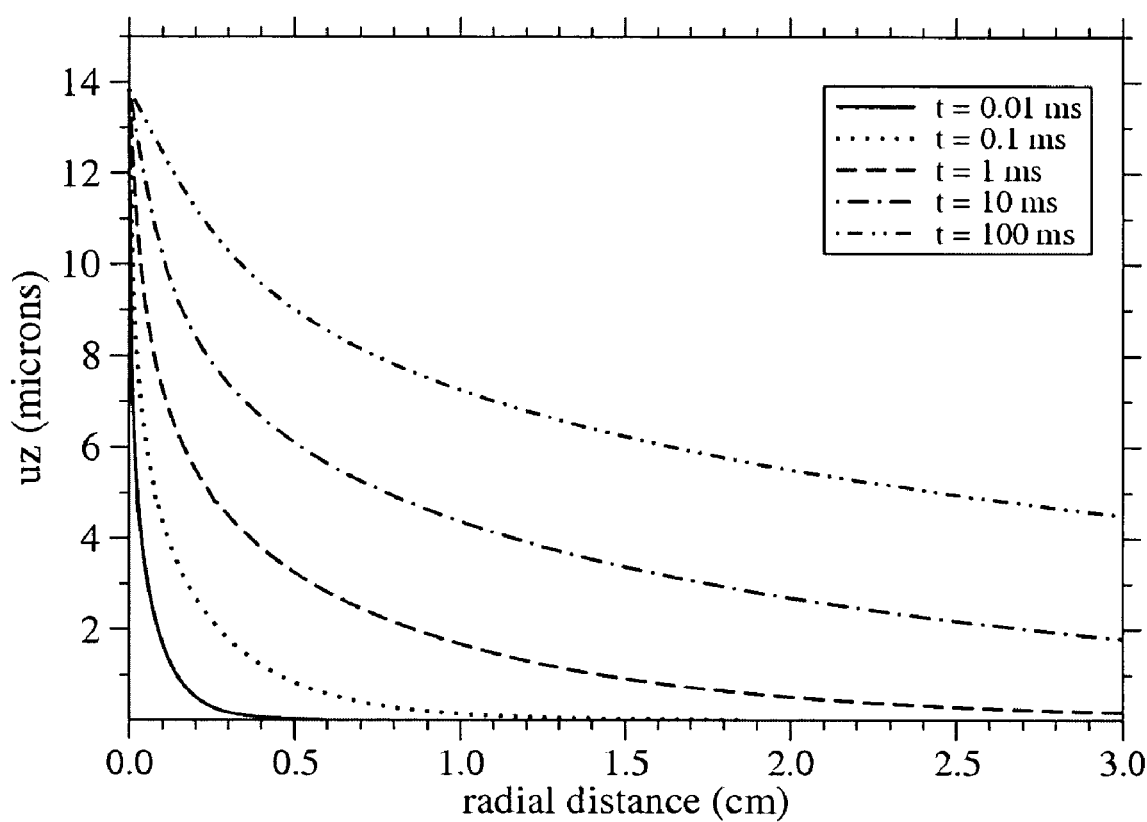
FIG. 5 shows the vertical displacement profile $u_z(r)$ (displacements measured in microns) of point on the surface at various times t after a steady state current of $I_0=0.1$ A has been turned on at r=0.

FIG. 5 shows the vertical displacement profile $u_z(r)$ (displacements measured in microns) of point on the surface at various times t after a steady state current of $I_0=0.1$ A has been turned on at r=0. The properties of the material correspond to a typical consolidated sandstone and are identical to those of FIG. 4.

The integral over $\theta_0$ is easily carried out and the substitution $x=r_0/r$ introduced into the integral over $r_0$ to obtain $$u_z(r, t) = \frac{LI_0}{2\pi\sigma\beta D} \int_0^{\pi} \frac{d\phi_0}{\cos^2\phi_0} \quad \text{(Eq. 30)}$$
$$\int_0^{\infty} dx \, \text{erfc}(xd) \left[\frac{1 + x^2 - x\cos\phi_0}{\sqrt{1 + x^2 - 2x\cos\phi_0}} - \sqrt{1 + x^2}\right]$$

All time and offset dependence (r,t) is confined to the dimensionless diffusion parameter $$d(r, t) = \frac{r}{\sqrt{4Dt}} \quad \text{(Eq. 31)}$$

The physical significance of this parameter is that $d(r,t)=1$ defines the approximate position of the diffusion front as it advances from the source point (r=0, t=0). Equation (30) is valid for all r>0. There is a single pole at (x=1, $\phi_0$=0) that dominates the contribution to $u_z$. The apparent singularity $\phi_0=\pi/2$ is removable (the integrand remains differentiable and finite at $\phi_0=\pi/2$). Nonetheless, a closed-form analytical result from these definite integrals is not, apparently, available. These integrals are therefore numerically performed using Simpson's rule.

The strains $\partial u_z/\partial r$ for points along the line φ=0 on the free surface θ=π/2 is then $$\frac{\partial u_z}{\partial r}(r, t) = \frac{LI_0}{2\sigma\beta D\sqrt{\pi Dt}} \int_0^{\pi} \frac{d\phi_0}{\cos^2\phi_0} \quad \text{(Eq. 32)}$$
$$\int_0^{\infty} dx \, x \exp(-x^2 d^2) \left[\frac{1 + x^2 - x\cos\phi_0}{\sqrt{1 + x^2 - 2x\cos\phi_0}} - \sqrt{1 + x^2}\right]$$

Figure 6:
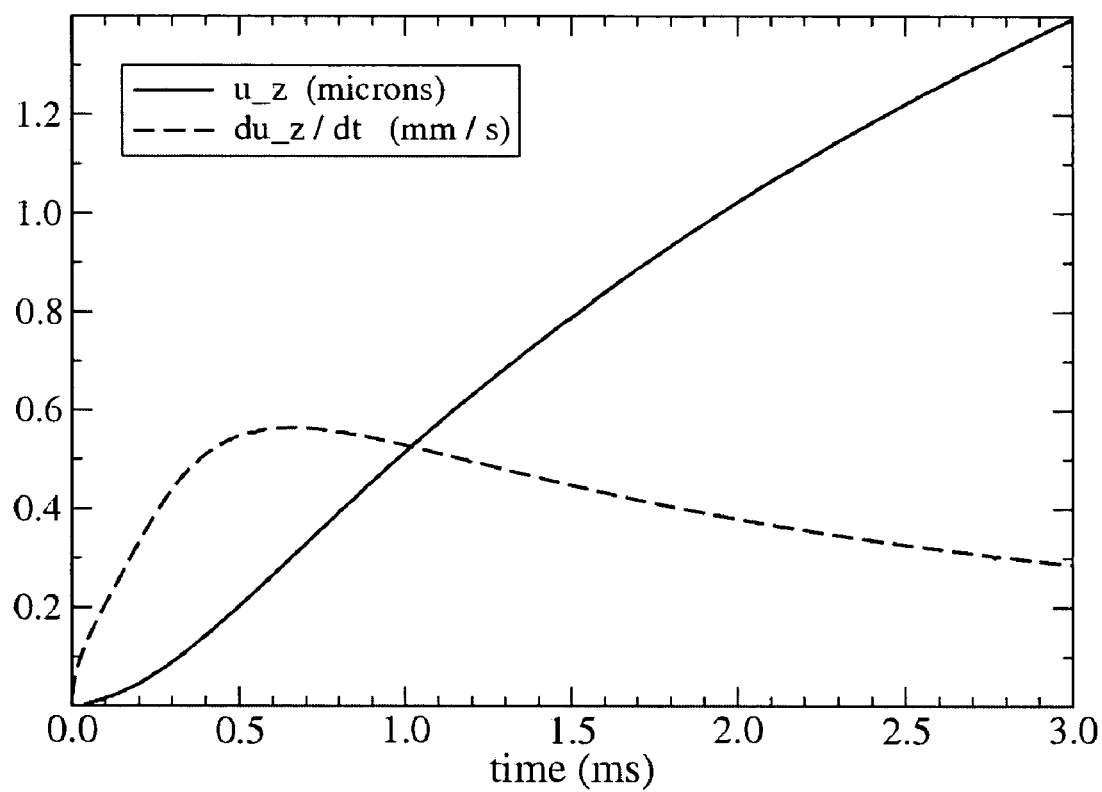
FIG. 6 shows the temporal evolution of the vertical displacement and the vertical particle velocity $\partial u_z/\partial t$ for an observation point a distance $r_0=2$ cm from the current injection point.

These integrals are again performed numerically. A typical displacement profile for a typical consolidated sandstone is presented in FIG. 6. As can be seen, FIG. 6 shows the temporal evolution of the vertical displacement and the vertical particle velocity $\partial u_z/\partial t$ for an observation point a distance $r_0=2$ cm from the current injection point. The physical properties are identical to those in FIG. 4 and the injected current is $I_0=0.1$ A. The vertical axis applies both to the displacements (microns) and particle velocities (millimeters/second).

Figure 7:
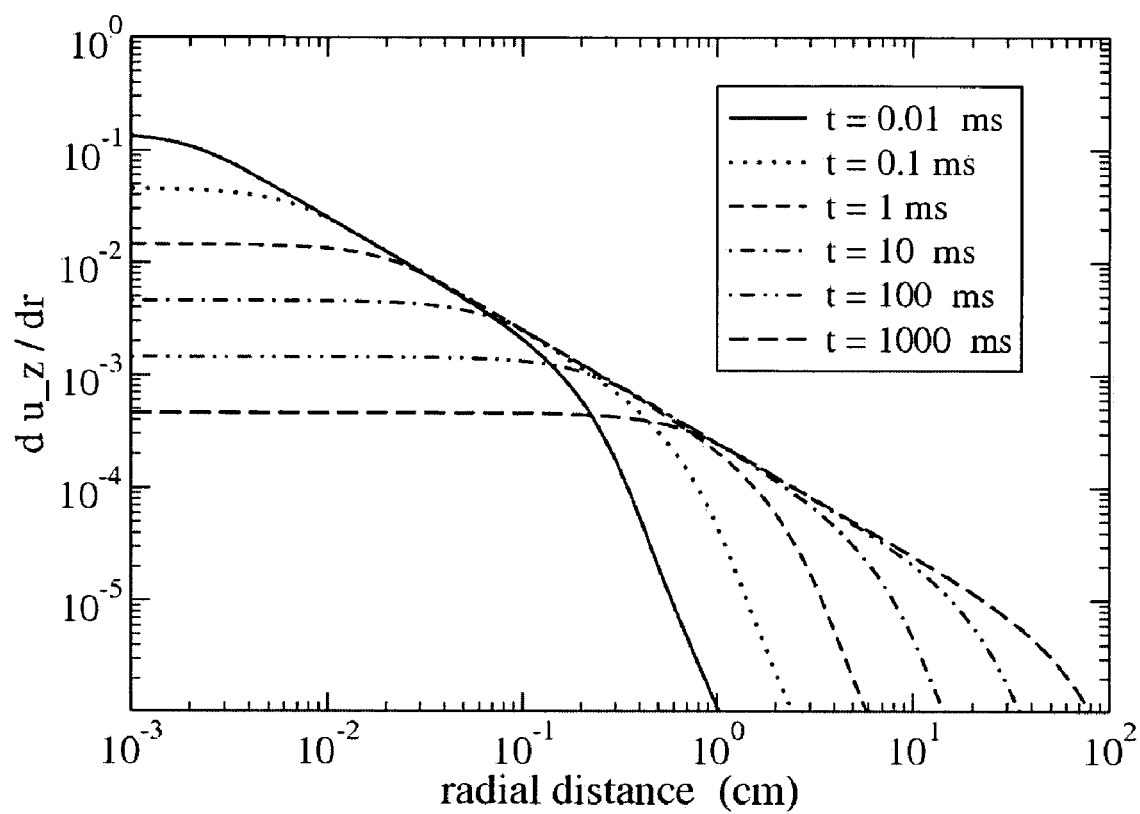
FIG. 7 shows the temporal evolution of both the strain and strain rate plotted at the fixed offset $r_0=2$ cm.

At the same fixed offset $r_0=2$ cm, the temporal evolution of both the strain and strain rate is plotted in FIG. 7. Note that both axes are logarithmic in this figure. These strain levels are quite measurable even for this relatively modest of injected current $I_0=0.1$ A.

Simple Inversion for the Fluid-Pressure Diffusivity D

In order to determine the fluid pressure diffusivity D from a strain measurement, one needs only to measure the inflection point in time where the strain rate $\partial u_z/\partial r \partial t$ goes through a maximum. This time $t_e$ at which the strain rate is a maximum along with distance $r_0$ from the injection point at which the strain is being measured will uniquely determine the diffusivity D. To obtain this result, (Eq. 32) is differentiated twice with respect to time and set to zero. One finds that the strain rate will be maximum when the function $f_e(d)$ (Eq. 33):
$$f_e(d) = \int_0^\pi \frac{d\phi_0}{\cos^2\phi_0} \int_0^\infty dx\, x \exp(-(xd)^2) \times \left[1 - 4(xd)^2 + \frac{4}{3}(xd)^4\right]\left[\frac{1 + x^2 - x\cos\phi_0}{\sqrt{1 + x^2 - 2x\cos\phi_0}} - \sqrt{1 + x^2}\right] \text{ equals zero.}$$

Figure 8:
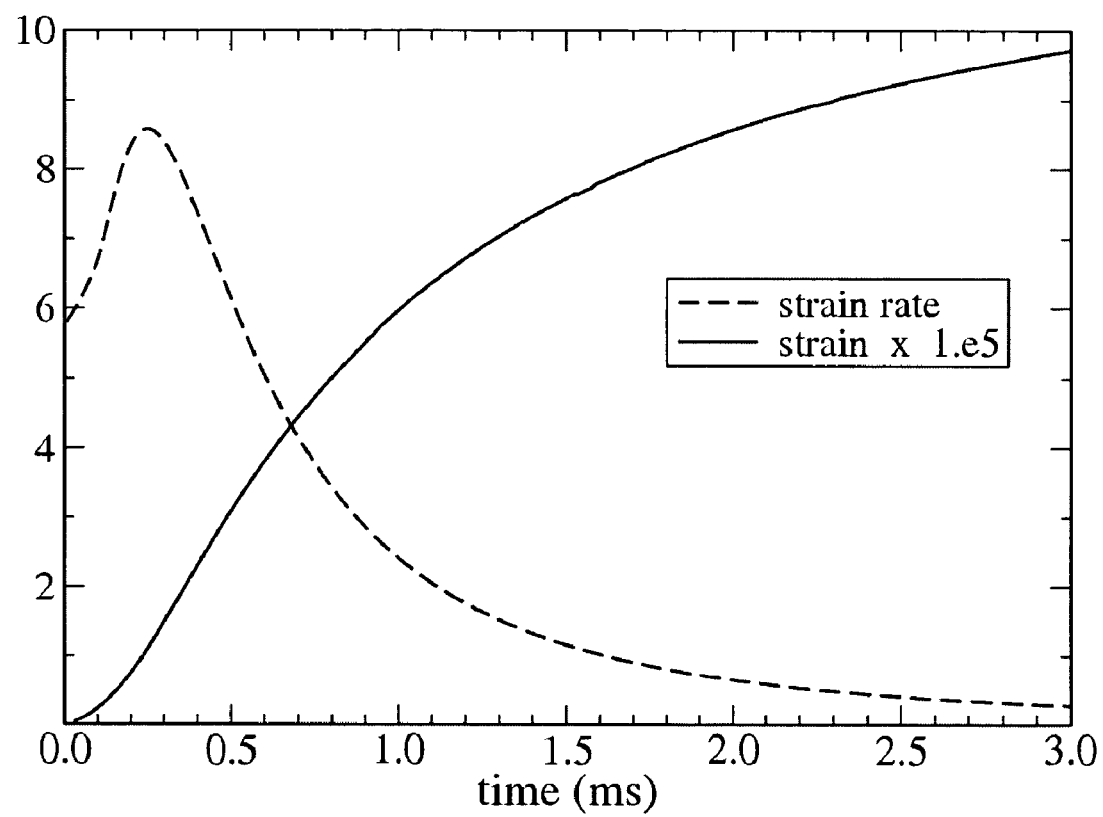
FIG. 8 shows the temporal evolution of the strain $\partial u_z/\partial r$ and strain rate $\partial^2 u_z/\partial r\partial t$ for an observation point at a distance $r_0=2$ cm from the current injection point.

FIG. 8 shows the temporal evolution of the strain $\partial u_z/\partial r$ and strain rate $\partial^2 u_z/\partial r \partial t$ for an observation point at a distance $r_0 = 2$ cm from the current injection point. The physical properties are identical to those in FIG. 5. The vertical axis applies both to the strain (after multiplication with $10^5$) and to the strain rate.

Figure 9A:
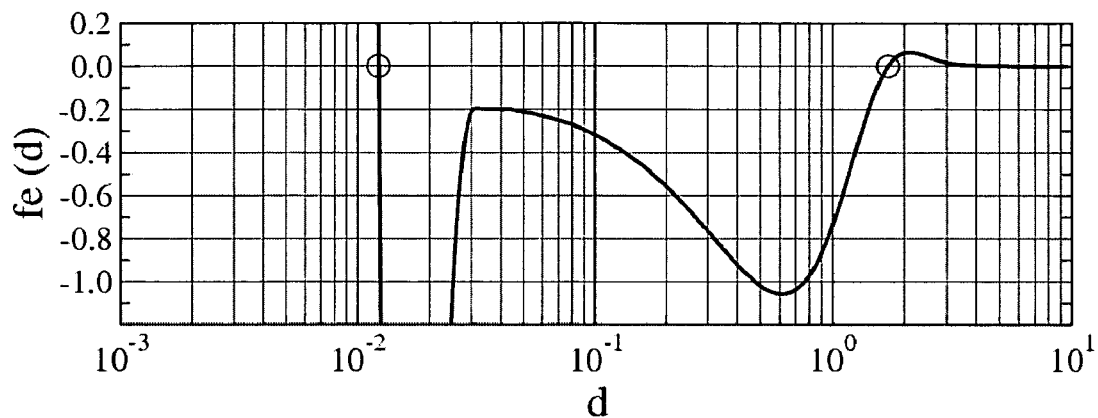
FIGS. 9(*a*) and 9(*b*) show the function $f_e(d)=0$ whose zeros correspond to the inflection point in time of the measured strain (maximum strain rate).
Figure 9B:
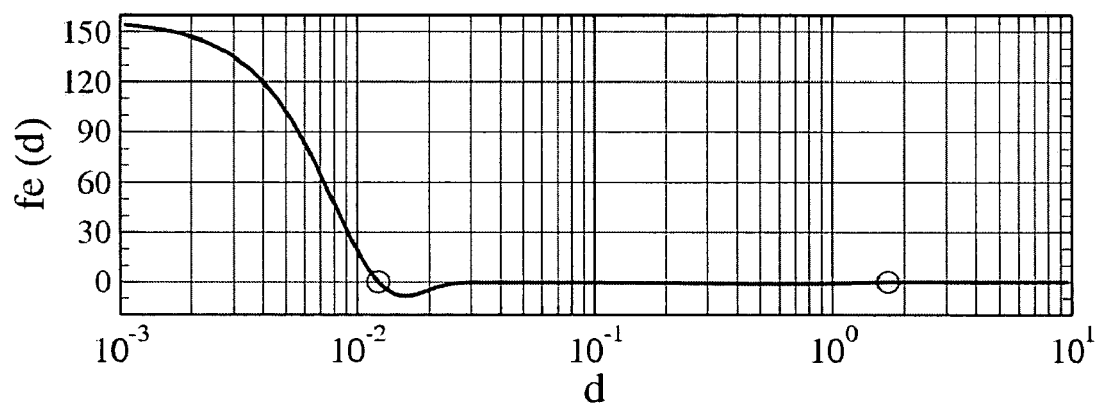

FIGS. 9(a) and 9(b) show the function $f_e(d)=0$ whose zeros correspond to the inflection point in time of the measured strain (maximum strain rate). FIG. 9(a) is simply a zoom of FIG. 9(b). There are two zero crossings denoted by the circles: one at d=0.01224 and another at d=1.70976. Furthermore, $\lim_{d\to\infty} f_e(d) \to 0$. The zero of physical interest is d=1.70976.

Thus, given the two definite zeros of the equation $f_e(d)=0$, at d=0.01224 and at 1.70976, by comparing to FIG. 8, it is easily shown the root at $d=d_e=1.70976$ is the one corresponding to strain rate. Thus, the diffusivity D of the material may be obtained from (Eq. 31) as $$D = \frac{r_0^2}{4d_e^2 t_e} = \frac{r_0^2}{11.6931 t_e} \quad \text{(Eq. 34)}$$

The strain rate maximum is more peaked in time than the particle-velocity maximum so that the inflection point is, in principle, more accurately determinable. However, it may sometimes be more convenient and even more accurate to measure particle velocity using Doppler-shifted laser beams or piezo ceramic transducers used for micro/nano positioning than to measure strain with a strain gauge and take the time derivative to obtain the strain rate. Accordingly, if the displacement or particle velocity at a point $r_0$ on the surface is being monitored (instead of the strain), the upon differentiating $u_z$ twice with respect to time, one obtains that the particle velocity will be maximum when the function $f_u(d)$ (Eq. 35):
$$f_u(d) = \int_0^\pi \frac{d\phi_0}{\cos^2\phi_0} \int_0^\infty dx\, x \exp(-(xd)^2) \times \left[1 - \frac{2}{3}(xd)^2\right]\left[\frac{1 + x^2 - x\cos\phi_0}{\sqrt{1 + x^2 - 2x\cos\phi_0}} - \sqrt{1 + x^2}\right]$$

is zero. There is only one definite zero of $f_u(d)=0$ and this occurs at $d_u=1.25793$. Thus, if the time $t_u$ at which the particle velocity is maximum, is measured at a distance $r_0$ from the injection electrode, one obtains the fluid pressure diffusivity using $$D = \frac{r_0^2}{4d_u^2 t_u} = \frac{r_0^2}{6.32955 t_u} \quad \text{(Eq. 36)}$$

In relatively stiff material for which $K_D \gg K_f$, instead of using (Eq. 14), one can use the often-made approximation $$D \approx \frac{k}{\phi} \frac{K_f}{\eta} \quad \text{(Eq. 37)}$$

And thus, the permeability k can be retrieved.

Advantages of embodiments of the present invention include one or more of the following. In one or more embodiments, a method is provided that is able to continuously measure the permeability of porous rock directly with accuracy from a downhole tool. In addition to its value in the assessment of the quality and quantity of water or oil reservoirs, rock diffusivity/permeability is very important in determining at what rate and at what cost these fluids can be produced from boreholes.

Diffusivity may be determined according to one or more embodiments of the invention by measurements of a step injection electrical current at an electrode on the borehole wall and measuring the displacement or the strain with respect to time. The method to determine the fluid-pressure diffusivity/permeability involves locating the point in time at which the second time derivative of either displacement or strain goes to zero; this time depends on the fluid pressure diffusivity of the material and the known distance from the injection point to strain/displacement gauges. The measurement of the inflection point in time provides a rapid (less than milliseconds) non-invasive means for measuring the fluid-pressure diffusivity of the porous material.

In one or more embodiments, instead of measuring pressure, the displacement or strain at the borehole wall is measured with a classical displacement or strain gauge or by other displacement sensor, such as, Doppler-shifted laser beams or by piezo ceramic transducers used for micro/nano positioning. By analyzing the spectrum of the recorded particle velocity (piezo electric transducer), particle acceleration (accelerometer), or strain, the ratio of the mechanical-response spectrum to the electrical-current spectrum at known offset can provide a measurement of fluid-pressure diffusivity.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A method of determining a fluid-pressure diffusivity in a borehole (12), comprising:

injecting an electrical current (16) into a point on a wall of the borehole (12);

measuring (18) at least one of strain, particle velocity, and particle acceleration at a fixed distance from the point of injection of the electrical current over time; and determining the fluid-pressure diffusivity based on the measured at least one of strain, particle velocity, and particle acceleration over time.

2. The method of claim 1, further comprising:

measuring (18),(20) at least one of strain, particle velocity, and particle acceleration at a plurality of fixed distances from the point of injection of the electrical current over time; and determining the fluid-pressure diffusivity based on the plurality of measured at least one of strains, particle velocities, and particle accelerations over time.

3. The method of claim 1, wherein the determining of the fluid-pressure diffusivity comprises locating a point in time at which a second time derivative of the measured at least one of strain, particle velocity, and particle acceleration is zero.

4. The method of claim 1, wherein the at least one of strain, particle velocity, and particle acceleration is measured (18) with a Doppler-shifted laser displacement sensor.

5. The method of claim 1, wherein the at least one of strain, particle velocity, and particle acceleration is measured (18) with a piezo ceramic transducer.

6. The method of claim 1, wherein a waveform of the injected current is a simple step function.

7. The method of claim 1, wherein the injected current is 0.1 A.

8. The method of claim 1, wherein the fixed distance is 2 cm.

9. The method of claim 1, further comprising:

mounting an electrode (16) on a pad (14);

mounting a measurement device (18) on the pad (14) a fixed distance from the electrode (16);

disposing the pad (14) against the wall of the borehole (14) to facilitate the electrode (16) injecting the electrical current and the measurement device (18) measuring at least one of strain, particle velocity, and particle acceleration over time.

10. The method of claim 9, further comprising:

mounting a second measurement device (20) on the pad (14) a second fixed distance from the electrode (16);

disposing the pad (14) against the wall of the borehole (12) to facilitate the second measurement device (20) measuring at least one of strain, particle velocity, and particle acceleration over time.

11. An apparatus for determining a fluid-pressure diffusivity in a borehole (12), comprising:

an electrode (16); and a measurement device (18) disposed a fixed distance from the electrode (16);

wherein the electrode (16) injects an electrical current into a point on a wall of the borehole (12), wherein the measurement device (18) measures at least one of strain, particle velocity, and particle acceleration at the fixed distance from the point of injection of the electrical current over time; and wherein the fluid-pressure diffusivity is determined based on the measured at least one of strain, particle velocity, and particle acceleration over time.

12. The apparatus of claim 11, wherein the electrode (16) and the measurement device (18) are mounted on a pad (14).

13. The apparatus of claim 11, wherein the determining of the fluid-pressure diffusivity comprises locating a point in time at which a second time derivative of the measured at least one of strain, particle velocity, and particle acceleration is zero.

14. The apparatus of claim 11, wherein the measurement device (18) is a Doppler-shifted laser displacement sensor.

15. The apparatus of claim 11, wherein the measurement device (18) is a piezo ceramic transducer.

16. The apparatus of claim 11, wherein a waveform of the injected current is a simple step function.

17. The apparatus of claim 11, wherein the injected current is 0.1 A.

18. The method of claim 11, wherein the fixed distance is 2 cm.

19. The apparatus of claim 11, further comprising:

a second measurement device (20) disposed a second fixed distance from the electrode (16);

wherein the second measurement device (20) measures at least one of strain, particle velocity, and particle acceleration at the second fixed distance from the point of injection of the electrical current over time; and wherein the fluid-pressure diffusivity is determined based on the second measured at least one of strain, particle velocity, and particle acceleration over time.

20. The apparatus of claim 19, wherein the electrode (16), the measurement device (18), and the second measurement device (20) are mounted on a pad (14).

21. An apparatus (5) for determining a fluid-pressure diffusivity in a borehole (12), comprising:

means for injecting (16) an electrical current into a point on a wall of the borehole (12); and means for measuring (18) at least one of strain, particle velocity, and particle acceleration at a fixed distance from the point of injection of the electrical current over time;

wherein the fluid-pressure diffusivity is determined based on the measured at least one of strain, particle velocity, and particle acceleration over time.

22. The apparatus (5) of claim 21, further comprising:

means for measuring (18),(20) at least one of strain, particle velocity, and particle acceleration at a plurality of fixed distances from the point of injection of the electrical current over time; and means for determining the fluid-pressure diffusivity based on the plurality of measured at least one of strains, particle velocities, and particle accelerations over time.

23. The apparatus (5) of claim 21, wherein the determining of the fluid-pressure diffusivity comprises locating a point in time at which a second time derivative of the measured at least one of strain, particle velocity, and particle acceleration is zero.

24. The apparatus (5) of claim 21, wherein a waveform of the injected current is a simple step function.

25. The apparatus (5) of claim 21, wherein the injected current is 0.1 A.

26. The apparatus (5) of claim 21, wherein the fixed distance is 2 cm.

27. A logging tool (5) for determining a fluid-pressure diffusivity in a borehole (12), comprising:

an electrode (16) mounted on a pad (14); and a measurement device (18) mounted on the pad (14) a fixed distance from the electrode (16);

wherein the pad (14) is disposed against a wall of the borehole (12) so as to facilitate the electrode (16) injecting an electrical current into a point on a wall of the borehole (12) and the measurement device (18) measures at least one of strain, particle velocity, and particle acceleration at the fixed distance from the point of injection of the electrical current over time;

wherein the electrode (16) injects an electrical current into the point on a wall of the borehole (12);

wherein the measurement device (18) measures at least one of strain, particle velocity, and particle acceleration at the fixed distance from the point of injection of the electrical current over time; and wherein the fluid-pressure diffusivity is determined based on the measured at least one of strain, particle velocity, and particle acceleration over time; and wherein the determining of the fluid-pressure diffusivity comprises locating a point in time at which a second time derivative of the measured at least one of strain, particle velocity, and particle acceleration is zero.

28. The logging tool of claim 27, wherein the measurement device (18) is a Doppler-shifted laser displacement sensor.

29. The logging tool of claim 27, wherein the measurment device (18) is piezo ceramic transducer.

30. The logging tool of claim 27, wherein a waveform of the injected current is a simple step function.

31. The logging tool of claim 27, wherein the injected current is 0.1 A.

32. The logging tool of claim 27, wherein the fixed distance is 2 cm.

* * * * *